US012778468B2

(12) United States Patent
Riviere et al.

(10) Patent No.: US 12,778,468 B2
(45) Date of Patent: Nov. 3, 2026

(54) METHOD FOR DETECTING A QUANTITY OF NO PRODUCED BY THE SUBJECT UNDER TEST, AND APPARATUS FOR CARRYING OUT SAID METHOD

(71) Applicant: NOPTRACK, Castres (FR)

(72) Inventors: Philippe Riviere, Toulouse (FR); Luc Vialard, Toulouse (FR); Yoann Perez, Sarrancolin (FR); Frederic Daumas, Pinsaguel (FR); Jean-Christophe Aubagnac, Saint-Jean (FR); Marc Labrunee, Toulouse (FR); Gilles Favre, Cugnaux (FR); Christian Amatore, Paris (FR)

(73) Assignee: NOPTRACK, Castres (FR)

( * ) Notice: Subject to any disclaimer, the term of this patent is extended or adjusted under 35 U.S.C. 154(b) by 458 days.

(21) Appl. No.: 17/058,588

(22) PCT Filed: May 28, 2019

(86) PCT No.: PCT/FR2019/051261
§ 371 (c)(1),
(2) Date: Nov. 24, 2020

(87) PCT Pub. No.: WO2019/229380
PCT Pub. Date: Dec. 5, 2019

(65) Prior Publication Data
US 2021/0137421 A1 May 13, 2021

(30) Foreign Application Priority Data
May 28, 2018 (FR) ...................................... 1854495

(51) Int. Cl.
*A61B 5/1468* (2006.01)
*A61B 5/00* (2006.01)
*A61B 5/145* (2006.01)

(52) U.S. Cl.
CPC ........ *A61B 5/1468* (2013.01); *A61B 5/14542* (2013.01); *A61B 5/6801* (2013.01); *A61B 2562/0219* (2013.01)

(58) Field of Classification Search
CPC ........ A61B 5/14517; A61B 2562/0219; A61B 5/6801; A61B 5/14542; A61B 5/1468;
(Continued)

(56) References Cited

U.S. PATENT DOCUMENTS 6,233,471 B1 * 5/2001 Berner ............... A61B 5/14532 600/347
8,435,570 B1 5/2013 Bryan
(Continued)

FOREIGN PATENT DOCUMENTS

CN 1802559 A 7/2006
CN 2807255 Y 8/2006
(Continued)

OTHER PUBLICATIONS

Jungil Choi et al. "Skin-interfaced systems for sweat collection and analytics" Science, vol. 4, No. 2, Feb. 16, 2018 (Feb. 16, 2018), p. eaar3921 DOI: 10.I 126/sciadv.aar3921 ISSN: 0036-8075, XP 055526287; http://dx.doi.org/10.1126/sciadv.aar3921.
(Continued)

*Primary Examiner* — Jason M Sims
*Assistant Examiner* — Ari S Padda
(74) *Attorney, Agent, or Firm* — Notaro, Michalos & Zaccaria P.C.

(57) ABSTRACT

A method of tracking a physiological state in a subject by studying the NO emission curve thereof measured by a sensing element on the epidermis thereof over a predefined activity sequence.

21 Claims, 5 Drawing Sheets

(58) Field of Classification Search
CPC ... A61B 5/1112; A61B 5/0004; A61B 5/1477; G16H 40/63
See application file for complete search history.

(56) References Cited

U.S. PATENT DOCUMENTS

| | | | | |
|---|---|---|---|---|
| 10,078,054 | B2 * | 9/2018 | Heywood | G01N 31/22 |
| 2004/0078219 | A1 | 4/2004 | Kaylor et al. | |
| 2006/0079740 | A1 | 4/2006 | Silver et al. | |
| 2008/0294026 | A1 * | 11/2008 | Arbault | A61B 5/442 600/345 |
| 2011/0106000 | A1 * | 5/2011 | Jones | A61P 33/00 424/94.4 |
| 2014/0073043 | A1 | 3/2014 | Holmes | |
| 2017/0141839 | A1 | 5/2017 | Chiodini et al. | |
| 2017/0143758 | A1 | 5/2017 | Greenberg et al. | |
| 2017/0184507 | A1 | 6/2017 | Heywood et al. | |
| 2017/0184564 | A1 * | 6/2017 | Liu | G01N 33/0037 |
| 2018/0028099 | A1 * | 2/2018 | Shekarriz | A61B 10/00 |
| 2018/0055373 | A1 * | 3/2018 | Kraiter | A61B 5/0022 |
| 2018/0064377 | A1 * | 3/2018 | Rogers | B01L 3/5027 |
| 2018/0340903 | A1 * | 11/2018 | Heikenfeld | A61B 5/00 |
| 2018/0353684 | A1 * | 12/2018 | Kim | G01N 33/66 |
| 2019/0013746 | A1 * | 1/2019 | Heinz | H02N 13/00 |
| 2019/0110722 | A1 * | 4/2019 | Ionescu | A61B 5/14517 |
| 2020/0306701 | A1 * | 10/2020 | Hammami | A61B 5/22 |

FOREIGN PATENT DOCUMENTS

| | | | |
|---|---|---|---|
| CN | 1997731 | A | 7/2007 |
| CN | 204538016 | U | 8/2015 |
| CN | 105140635 | A | 12/2015 |
| CN | 106415672 | A | 2/2017 |
| CN | 107278370 | A | 10/2017 |
| WO | 9808480 | A2 | 3/1998 |
| WO | 2016061362 | A2 | 4/2016 |

OTHER PUBLICATIONS

Yejin Ha et al. "Measurements of Location-Dependent Nitric Oxide Levels on Skin Surface in relation to Acupuncture Point" Evidence-Based Complementary and Alternative Medicine vol. 2012, Jan. 1, 2012 (Jan. 1, 2012), pp. 1-7 DOI: 10.1155/2012/781460 ISSN: I 741-427X, XP055524807; http://dx.doi.org/10.1155/2012/781460.

Albert Maarek et al. "Detection of neuropathy using a sudomotor test in type 2 diabetes" Degenerative Neurological and Neuromuscular Disease, Jan. 9, 2015 (Jan. 9, 2015), p. 1 DOI: 10.2147/DNND. S75857 ISSN: 1179-9900, XP055525495; http://dx.doi.org/10.2147/DNND.S75857.

Byeong Wan An et al. "Smart Sensor Systems for Wearable Electronic Devices" Polymers, vol. 9, No. 12, Jul. 25, 2017 (Jul. 25, 2017), p. 303 DOI: 10.3390/polym9080303 XP055526164; http://dx.doi.org/10.3390/polym9080303.

Youngmi Lee et al. "Improved Planar Amperometric Nitric Oxide Sensor Based on Platinized Platinum Anode. 1. Experimental Results and Theory When Applied for Monitoring NO Release from Diazeniumdiolate-Doped Polymeric Films—Analytical Chemistry (ACS Publications)" Jan. 1, 2004 (Jan. 1, 2004), Retrieved from the Internet: https://pubs.acs.org/doi/10.1021/ac035064h [retrieved on Nov. 22, 2018] XP055526149; https://pubs.acs.org/doi/10.1021/ac035064h.

Bruch-Gerharz D et al. Nitric oxide in human skin: current status and future prospects Journal of Investigative Dermatology, Elsevier, NL, vol. 110, No. 1, Jan. 1, 1998 (Jan. 1, 1998), pp. 1-7 DOI: 10.1046/J.1523-I 747.1998.00084.X ISSN: 0022-202X, XP002254968; https://www.jidonline.org/article/S0022-202X (15)37356-5.

Ma et al. "Evidence of enhanced non-enzymatic generation of nitric oxide on the skin surface of acupuncture points: An innovative approach in humans" Nitric Oxide: Biology and Chemistry, Academic Press, Amsterdam, NL, vol. 17, No. 2, Aug. 18, 2007 (Aug. 18, 2007), pp. 60-68 DOI: 10.1016/J.NIOX.2007.05.004 ISSN: 1089-8603, XP022207173; http://dx.doi.org/10.1016/j.niox.2007.05.004.

Mallika Bariya et al. "Wearable sweat sensors" Nature Electronics, vol. 1, No. 3, Mar. 1, 2018 (Mar. 1, 2018), pp. 160-171 DOI: 10.1038/s41928-018-0043-y ISSN: 2520-1131, XP055525597; http://dx.doi.org/10.1038/s41928-018-0043-y.

Johne Lewis et al. New method of sudomotor function measurement to detect microvascular disease and sweat gland nerve or unmyelinated C fiber dysfunction in adults with retinopathy Journal of Diabetes & Metabolic Disorders, Biomed Central Ltd, London, UK, vol. 16, No. 1, Jun. 12, 2017 (Jun. 12, 2017), pp. 1-10 DOI: 10./I 86/S40200-017-0307-5 XP021245874; http://dx.doi.org/10.1186/s40200-017-0307-5.

Yejin Ha et al. "Insertable NO/CO Microsensors Recording Gaseous Vasomodulators Reflecting Differential Neuronal Activation Level with Respect to Seizure Focus" ACS Chemical Neuroscience, US, vol. 8, No. 9, Jul. 5, 2017 (Jul. 5, 2017), pp. 1853-1858 DOI: 10.1021/acschemneuro.7b00141 ISSN: 1948-7193, XP055524923; http://dx.doi.org/10.1021/acschemneuro.7b00141.

Sai.Zitsa Anastasova et al. "A wearable multisensing patch for continuous sweat monitoring" Biosensors and Bioelectronics, Amsterdam, NL, vol. 93, Jul. 1, 2017 (Jul. 1, 2017), pp. 139-145 DOI: 10.1016/j.bios.2016.09.038 ISSN: 0956-5663, XP055482880; http://dx.doi.org/10.1016/j.bios.2016.09.038.

Richard Weller et al. Nitric Oxide Is Generated on the Skin Surface by Reduction of Sweat Nitrate Journal of Investigative Dermatology, vol. 107, No. 3, Sep. 1, 1996 (Sep. 1, 1996), pp. 327-331 DOI: 10.I I I I/1523-I 747.epl2363167 XP055205544; http://dx.doi.org/10.1111/1523-1747.ep12363167.

Kichang Lee et al. "Role of nitric oxide in methacholine-induced sweating and vasodilation in human skin" Journal of Applied Physiology, United States, Apr. 1, 2006 (Apr. 1, 2006), pp. 1355-1360, Retrieved from the Internet: https://pdfs.semanticscholar.org/c834/lf4a660265al 2e6e0bf87ba563ab9b9felce.pdf DOI: 10.I 152/japplphysiol.00122.2005 XP055525486; https://pdfs.semanticscholar.org/c834/1f4a660265a12e6e0bf87ba563ab9b9fe1ce.pdf or http://dx.doi.org/10.1152/japplphysiol.00122.2005.

Vincenzo F. Curto et al. "Real-time sweat pH monitoring based on a wearable chemical barcode micro-fluidic platform incorporating ionic liquids" Sensors and Actuators B: Chemical: International Journal Devoted to Research and Development of Physical and Chemical Transducers, NL, vol. 171-172, Aug. 1, 2012 (Aug. 1, 2012), pp. 1327-1334 DOI: 10.1016/j.snb.2012.06.048 ISSN: 0925-4005, XP055451404; http://dx.doi.org/10.1016/j.snb.2012.06.048.

Hnin Yin Yin Nyein et al. "A Wearable Microfluidic Sensing Patch for Dynamic Sweat Secretion Analysis" ACS Sensors, vol. 3, No. 5, May 9, 2018 (May 9, 2018), pp. 944-952 DOI: 10.1021/acssensors.7b00961 ISSN: 2379-3694, XP055525587; http://dx.doi.org/10.1021/acssensors.7b00961.

Kramer Ry An Met al. "Analytical determination and detection of individual odor signatures" Sensing Technologies for Global Health, Military Medicine, Disaster Response, and Environmental Monitoring II; and Biometric Technology for Human Identification IX, SPIE, 1000 20th St. Bellingham WA 98225-6705 USA, vol. 8371, No. 1, May 11, 2012 (May 11, 2012), pp. 1-14 DOI: 10.1117/12.919921 XP06000273; http://dx.doi.org/10.1117/12.919921.

Yejin Ha et al. "Amperometric Microsensors Monitoring Glutamate-Evoked In Situ Responses of Nitric Oxide and Carbon Monoxide from Live Human Neuroblastoma Cells" Sensors, vol. 17, No. 7, Jul. 19, 2017 (Jul. 19, 2017), p. 1661 DOI: 10.3390/sl 7071661 XP055524813; http://dx.doi.org/10.3390/s17071661.

GF Clough et al. "Measurement of nitric oxide concentration in human skin in vivo using dermal microdialysis" Experimental Physiology, GB, vol. 83, No. 3, May 1, 1998 (May 1, 1998), pp. 431-434DOI: 10.I I 13/expphysiol.1998.sp004126ISSN: 0958-0670, XP055526121; http://dx.doi.org/10.1113/expphysiol.1998.sp004126.

Luo Xiaojin et al. "A Wearable Amperometric Blosensor on a Cotton Fabric for Lactate" IEEE Electron Device Letters, IEEE Service Center, New York, NY, US, vol. 39, No. 1, Jan. 1, 2018 (Jan.

(56) References Cited

OTHER PUBLICATIONS 1, 2018), pp. 123-126, [retrieved on Dec. 26, 2017] DOI: 10.1109/LED.2017.2777474 ISSN: 0741-3106, XP011675011; http://dx.doi.org/10.1109/LED.2017.2777474.
International Search Report for corresponding PCT application No. PCT/FR2019/051261, mailed Oct. 9, 2019.
Choi, Jungil , "Skin-interfaced systems for sweat collection and analytics", Science Advances , Applied Sciences and Engineering, Feb. 16, 2018.
Chinese office action for corresponding Chinese application No. 2019800356271, dated Feb. 1, 2024, with English translation.
Office Action for Chinese Application No. 201980035627.1, Issued on Mar. 31, 2025.

* cited by examiner

METHOD FOR DETECTING A QUANTITY OF NO PRODUCED BY THE SUBJECT UNDER TEST, AND APPARATUS FOR CARRYING OUT SAID METHOD

The invention relates to a method and a device for detecting, in a dead or living human or animal or plant subject, for example a physiological state and/or a physiopathological state of the subject. The invention also relates to a self-contained device for measuring NO for the purpose of determining a physiological or physiopathological state of the subject such as for example diagnosing and/or preventing the appearance of pathologies linked to this molecule and/or monitoring therapeutic efficacy.

It is known that nitric oxide is a gas which constitutes an intercellular messenger. NO plays an important role in the protection against the appearance and progression of certain cardiovascular diseases, certain neurodegenerative diseases, pulmonary arterial hypertension, or else oncogenesis. Associated cardiovascular pathologies include hypercholesterolemia, hypertension and diabetes. The underlying disease for most cardiovascular diseases (cerebral vessels, coronary arteries, lower limb ischemia) is a dysfunctional endothelial system, which is associated with arteriosclerosis which may lead to thrombotic and ischemic pathologies.

The cardioprotective role of NO includes in particular regulation of tension and vascular tone, inhibition of platelet accumulation, leukocyte adhesion and the proliferation of smooth muscle fiber cells. NO is also involved in bronchial inflammation; in particular it has been measured that the concentration of NO is higher in the air exhaled from asthmatic subjects than from non-asthmatic subjects. It has also been observed that NO is involved, depending on its concentration, in the appearance or regression of tumors. It has also been observed that NO is involved in the pathology of Alzheimer's disease. All of the diseases affected by NO fall within long-term disorders, the annual cost of which becomes greater each year and requires tools for preventing and predicting the appearance of these diseases.

In physiology, nitric oxide is a very good indicator of muscle growth and/or distress and therefore of the monitoring of the physical training of athletes and also of any person who undertakes a physical activity. Thus, by measuring the production of nitric oxide, it is possible to avoid injuries due to overtraining and/or to promote the uptake of NO in order to promote muscle growth and increase sporting performance. This applies both to humans and animals.

In the case of a cardiovascular disease, devices currently in existence and the tools for prevention and prediction are either limited to an indirect measurement of the NO of the patient at rest, or limited to a direct measurement delayed by several hours relative to an observation of a pathological problem. In all cases, the measurements can only be carried out in a clinical environment.

According to the present invention, a device is proposed that enables a direct, continuous and immediate measurement of the NO in a biological liquid, such as sweat, on an epidermis, such as the skin, in a subject such as a patient or a mammal, in its everyday life or at the time of a medical prescription in a clinical setting, optionally over several days and under all environmental conditions, in particular as regards pressure, humidity and temperature. Such a device makes it possible to detect and deduce the development of a physiological or physiopathological state such as a risk of appearance of pathologies or therapeutic monitoring.

One subject of the present invention is a method for detecting, in a subject, in particular a human or animal or plant subject, the subject being dead or living, an amount of NO produced by said subject in the course of a sequence of a predefined activity state, characterized in that an investigation zone of an epidermis of said subject is chosen, the production of NO dissolved in a biological liquid originating from the epidermis is tracked therein, directly and continuously, by means of a device formed of a first part, borne by said investigation zone and held thereon in a leak-tight manner, this first part being attached to a sensing element, which carries out the detection of the NO by means of an electrochemical sensor, and that, owing to an energy generator associated with said sensing element, a signal is sent by said electrochemical sensor, the reading of which signal enables the desired detection.

The expression "NO in a biological liquid" is understood to mean that the NO is dissolved in a biological liquid.

The term "epidermis" is understood to mean the surface plant tissue forming a protective layer of the aerial parts of a plant or the surface layer of the skin in humans and animals.

The expression "biological liquid originating from the epidermis" is understood to mean any liquid produced by the subject and excreted via or by the epidermis of the subject. This biological liquid is for example the exudate in plants or the sweat in humans and animals.

The expression "in a leak-tight manner" is understood to mean that gases, liquids and microorganisms such as bacteria or viruses located outside of the investigation zone cannot enter into the investigation zone. The leak-tightness of the contact between the first part and the investigation zone ensures that the NO detected originates from the biological liquid produced by the investigation zone, and not from a flow coming from the outside.

The term "sequence" is understood to mean a time sequence i.e. a time interval. The expression "predefined activity state" is understood to mean the state in which the subject is in, for example carrying out a muscle exercise, sleeping, sitting down, running, immobile, or even dead, etc.

According to one embodiment, the method makes it possible to detect at least one parameter associated with a physiological state or a pathology.

According to one embodiment, the first part comprises a fibrous body in order to convey the biological liquid from the investigation zone to the sensing element by means of capillary forces.

According to one embodiment, the first part further comprises a filter configured to filter the biological liquid at an inlet of the sensing element in order to avoid distorting the detection of NO by interfering elements contained in the biological liquid.

According to one embodiment, the filter is a eugenol-type membrane.

According to some embodiments, the fibrous body may be a woven material, and a nonwoven material such as cotton.

In an alternative form of the method, use is made of at least one electrochemical sensor, which provides a signal as a result of an electrochemical measurement taken using the biological liquid, in particular sweat or exudate, produced by the subject in the investigation zone, as electrolyte between two working electrodes borne by an insulating planar support.

According to one embodiment, the insulating planar support comprises a material chosen from elastomers such as polydimethylsiloxane (PDMS), polyimides, epoxy resins and parylene.

Provision may be made, in the method according to one alternative form of the invention, for a reference electrode to be connected to the two working electrodes.

According to one embodiment, the reference electrode is a silver chloride (AgCl) electrode.

Provision may also be made for the sensing element to comprise a plurality of similar electrochemical sensors, the signals of which are combined to improve the output signal.

Provision may be made for the pattern of the electrodes relative to their support to follow a Hilbert curve, in order to improve the power of the output signal per unit area of the support.

According to one embodiment, the pattern of the electrodes relative to their support may follow another type of curve chosen from a Peano curve, a Sierpiński curve, a Moore curve and a Lebesgue curve, also for the purpose of improving the strength of the output signal per unit area of the support.

Provision may be made for the measurements to be carried out in line with orifices provided in the planar support, which is in line with the conductive patterns of the electrodes.

In an advantageous embodiment, the electrodes consist of metal deposits, in particular deposits of silver (Ag), gold (Au), platinum (Pt), and platinum black, or graphene deposits doped by nanoparticles of silver (Ag) or of gold (Au), the nanoparticles being functionalized by binders of NO, in particular guanylyl-cyclase or porphyrins.

According to one embodiment, metal deposits of gold are produced as clusters or produced by following a precise pattern, for example a hexagonal pattern.

For one implementation of the method according to invention, provision may be made for the device to further comprise a second part positioned above the first part, the second part containing electronics for receiving the raw measurements from the electrochemical sensor, converting them into an NO concentration and ensuring the transmission of the signal possibly with other parameters linked to the environment.

Provision may be made, in the method according to the invention, for the device to carry out and transmit measurements at a frequency that is a function of the activity state of the subject, this state being tracked by means of a gyroscopic and/or accelerometric module of the second part of the device.

According to one embodiment, the device comprises a geolocation module.

The invention also relates to a detection device for detecting, in a subject, an amount of NO produced by said subject in the course of a sequence of a predefined activity state, said device comprising a first part intended to be borne by an investigation zone of an epidermis of said subject and held thereon in a leak-tight manner in order to track, directly and continuously, the production of NO in a biological liquid originating from the epidermis, the first part being attached to a sensing element, which carries out the detection of NO by means of an electrochemical sensor, and a second part configured to send, owing to an energy generator associated with said sensing element, a signal, the reading of which enables the desired detection.

Provision may be made for the sensing element to provide the signal as a result of an electrochemical measurement taken using the biological liquid, produced by the subject in the investigation zone, as electrolyte between two working electrodes borne by an insulating planar support.

In an abovementioned alternative form, provision may be made for a reference electrode to be connected to the two working electrodes.

According to one embodiment, the insulating planar support comprises at least one microchannel so as to guide the biological liquid to the electrochemical sensor.

Provision may be made for the sensing element to comprise a plurality of similar electrochemical sensors, the signals of which are combined to improve the output signal.

According to one embodiment, the sensing element comprises a plurality of electrochemical sensors distributed in a plurality of sensing units and in that each sensing unit is configured to detect at least one chemical species. The sensing element may then detect several different chemical species.

According to one embodiment, the insulating planar support comprises a plurality of microchannels, and each channel comprises a sensing unit.

Provision may be made, in the device according to the invention, for the pattern of the electrodes relative to their support to follow a Hilbert curve in order to improve the strength of the output signal per unit area of the support.

In such a device, the measurements are carried out in line with orifices provided in the planar support, which is in line with the conductive patterns of the electrodes.

Provision may be made, in the device according to the invention, for the working electrodes to consist of metal deposits, in particular deposits of silver (Ag), gold (Au), platinum (Pt), and platinum black, or graphene deposits doped by nanoparticles of silver (Ag) or of gold (Au), the nanoparticles being functionalized by binders of NO, in particular guanylyl-cyclase or porphyrins.

According to one embodiment, the first part comprises a fibrous body in order to convey the biological liquid from the investigation zone to the sensing element by means of capillary forces.

According to one embodiment, the first part further comprises a filter configured to filter the biological liquid at an inlet of the sensing element in order to avoid distorting the detection of NO by interfering elements contained in the biological liquid.

Provision may be made, in the device according to the invention, for the second part to be positioned above the first part, the second part containing electronics for receiving the raw measurements from the electrochemical sensor, for converting them into an NO concentration and ensuring the transmission of the signal possibly with other parameters linked to the environment.

Provision may be made, in the device according to the invention, for the device to carry out and transmit measurements at a frequency that is a function of the activity state of the subject, this state being tracked by means of a gyroscopic and/or accelerometric module of the second part of the device.

According to one embodiment, the device comprises a geolocation module.

In order to make the subject of the invention easier to understand, a description will be given hereinbelow, by way of purely illustrative and nonlimiting example, of one embodiment thereof, depicted in the appended drawing. In this drawing.

Figure 7:
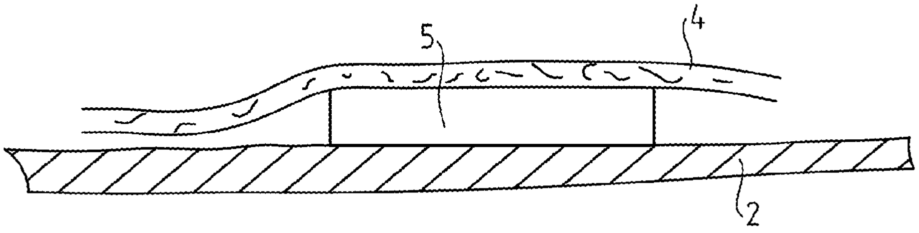
Figure 8:
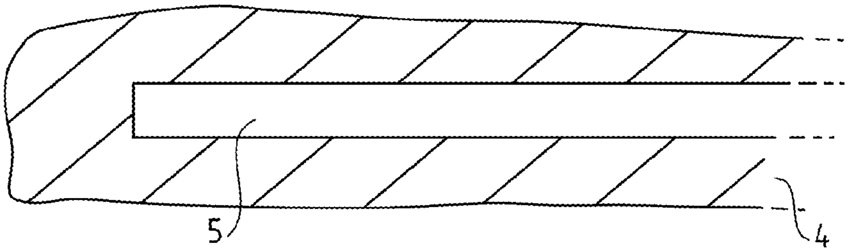
Figure 9:
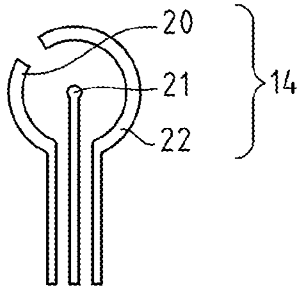
Figure 10:
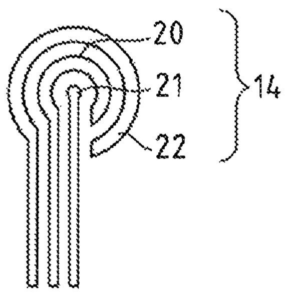
Figure 11:
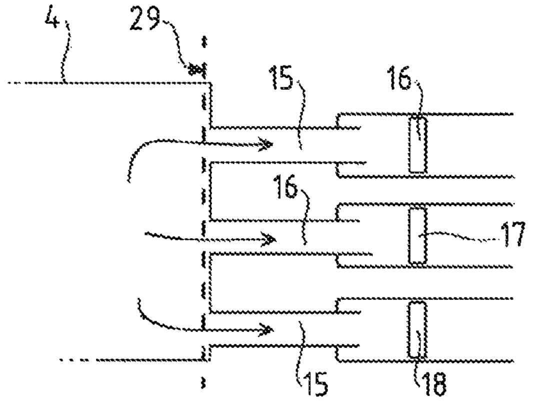
Figure 12:
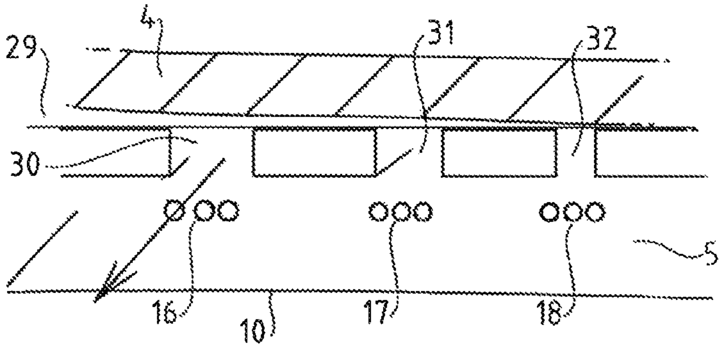

FIG. 7 schematically depicts a first arrangement of the fibrous body and of the sensing element of the device;

FIG. 8 schematically depicts a second arrangement of the fibrous body and of the sensing element of the device;

FIG. 9 schematically depicts an electrochemical sensor of the sensing element comprising three electrodes according to a first embodiment;

FIG. 10 schematically depicts an electrochemical sensor of the sensing element comprising three electrodes according to a second embodiment;

FIG. 11 is a functional schematic depiction of a micro-hydraulic circuit arranged in the sensing element;

FIG. 12 is a cross-sectional view of the sensing element according to one embodiment.

Figure 1:
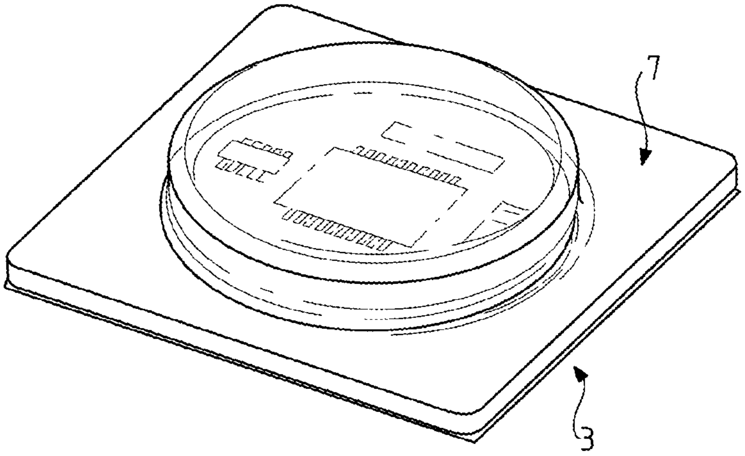
FIG. 1 depicts, in perspective, an external general view of a detection device according to the invention.
Figure 2:
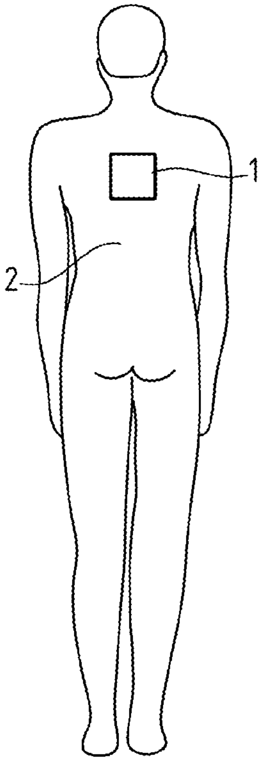
FIG. 2 depicts an overall view of a subject on whom a device according to the invention has been put in place.
Figure 6:
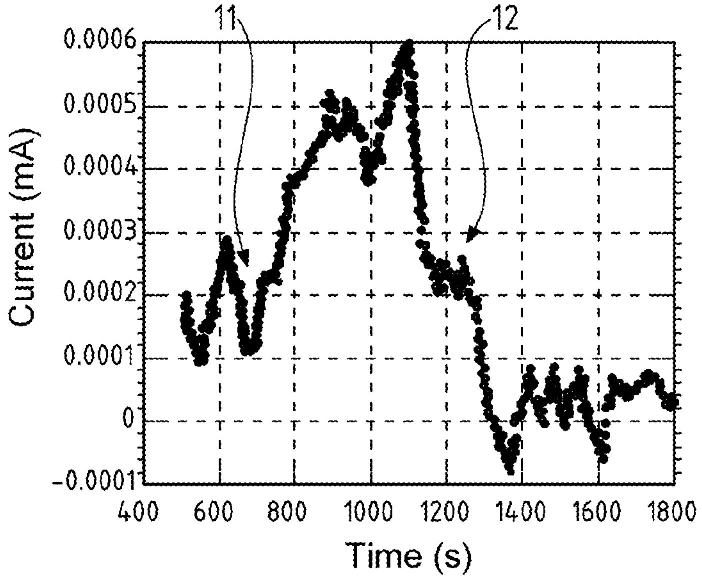
FIG. 6 depicts a graph obtained from a healthy subject equipped with a device according to the invention, as indicated in FIG. 2.

With reference to the drawing, it is seen that the detection device according to the invention is denoted by 1 throughout; it is intended to take a quantitative measurement of NO in a healthy human subject. In the example described, the subject carries out a physical activity by the use of a bicycle corresponding to a power of 160 W. As FIG. 6 shows, the detection of NO is carried out from the start of the test (point 11) until the end of the test (point 12), i.e. for a time sequence of around 500 seconds. With reference to FIG. 1, the device 1 is overall in the form of a self-adhesive part that takes, in the example, the form of a self-adhesive pad, that can be positioned directly on the skin of the subject. In one embodiment that is not illustrated, the self-adhesive part is a self-adhesive dressing.

The device according to the invention comprises a fastening base 3 made of a biocompatible and adhesive flexible material; this base ensures that the complete device is held on the skin; the central part 4*a* of the base 3 is a circular recess where the first part of the device is positioned, which makes it possible to track the production of NO in the investigation zone of the skin of the subject. The circular recess 4*a* therefore enables the positioning of the first part of the measurement device directly on the skin 2 of the subject. The recess 4*a* may take another shape, for example chosen from ellipse, triangle, rectangle, square or polygon.

This first part comprises a fibrous body 4 which is attached to a sensing element 5 which it surmounts, as illustrated in FIG. 7, or which it envelopes, as illustrated in FIG. 8, to constitute the base of a stack. The fibrous body fulfills the function of conveying the sweat produced in the investigation zone to the sensing element 5 so that the nitric oxide dissolved therein is detected, then of discharging the sweat once the measurement has been carried out.

A filter 29 may optionally be arranged between the fibrous body 4 and the inlet(s) of the sensing element 5. The function of the filter 29 is to filter the sweat to prevent certain elements naturally contained therein from disrupting the measurement of the NO dissolved in the sweat. These interfering elements are for example peroxynitrite ($ONOO^-$) or hydrogen peroxide ($H_2O_2$).

The sensing element 5 detects the NO by means of one or more electrochemical sensors 14, which will be defined below. The sensor sends its information to a converter 6*a*, which itself supplies a processor 6*b*, powered by an energy generator 6*d* associated with said sensing element 5. The processor 6*b* supplies a radiocommunication system 6*c*, which sends the information to instrumentation which is capable of converting this information into a graph such as the one depicted in FIG. 6.

In this FIG. 6, the portion constituting the measurement of the NO produced during the effort by the subject is the portion which is between points 11 and 12 of the graph. The whole of the graph of FIG. 6 between points 11 and 12 corresponds to one parameter. Depending on the value of this parameter, it is possible to link a pathology such as arteriosclerosis. It is also possible to accompany the management of a physiological function such as the monitoring of the bioavailability of L-arginine. Specifically, the natural precursor of NO in an organism is an amino acid called L-arginine. The human body can produce NO in response to an effort only within the limits of its store of L-arginine. Consequently, the device also makes it possible to predict the moment when the subject will no longer be able to manage his/her vasodilation, and therefore the risk of becoming injured.

Figure 4:
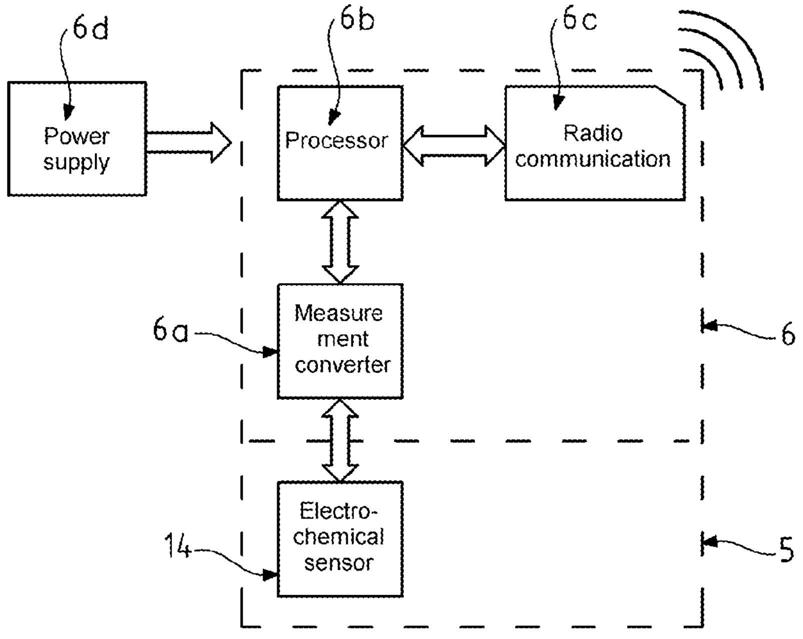
FIG. 4 depicts a block diagram corresponding to the operation of the device from FIG. 3.

All the components carrying out the various functions depicted in FIG. 4 are assembled together in an embedded electronics system, denoted by 6 in its entirety. The constituents 4, 5 and 6 form a stack, which is held on the skin of the subject by means of a flexible and watertight envelope of silicone type, denoted by 7 in its entirety.

The embedded electronics system of the component 6 carries out the functions of control of the members of the sensing element 5; it also comprises a gyroscopic and accelerometric unit in order to know the orientation and the movements of the subject and also the start and the end of the activity sequence of the subject, and a temperature sensor to measure the temperature of the skin. It is useful to know the temperature of the skin in order to be able to correlate the temperature and the dilation of the vessels.

Figure 5:
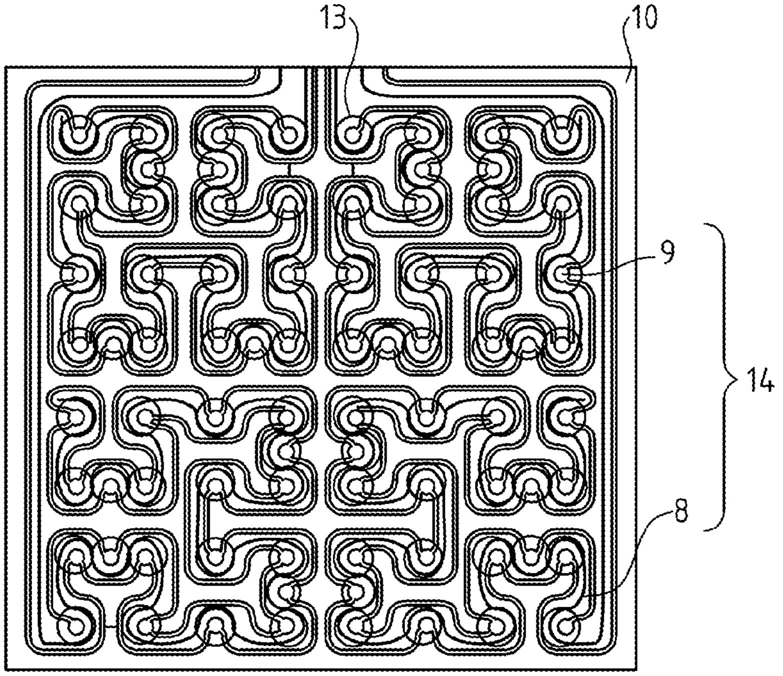
FIG. 5 depicts a top view of a planar support bearing two electrodes put in place according to Hilbert curves.

The sensing element of the example described is electrochemical; the one depicted in FIG. 5 comprises an electrochemical sensor 14 and an insulating planar support 10 made of polyimide. The electrochemical sensor comprises two electrodes 8 and 9 positioned on one side of the insulating planar support 10 and between which is the sweat produced by the subject in the investigation zone, i.e. in line with the stack 4, 5, 6. In the sensing element depicted in FIG. 5, it is seen that there are four identical units each making it possible to obtain an NO measurement. Installing several sensing units advantageously makes it possible to obtain a cutaneous map of NO production within the zone covered.

Figure 3:
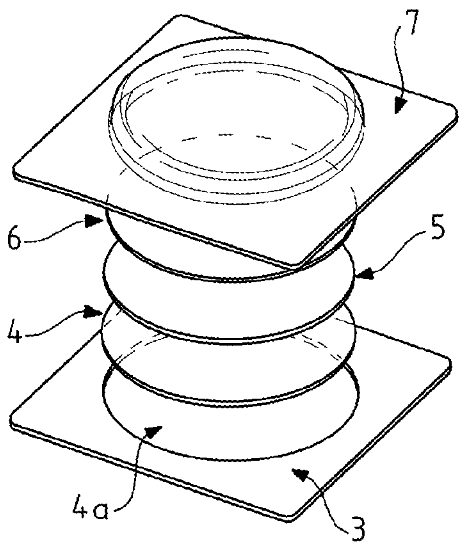
FIG. 3 depicts an exploded view of the device from FIG. 1.

With reference to FIG. 7, the fibrous body 4 and the sensing element 5 are arranged differently from FIG. 3. The insulating planar support 10 is positioned directly on the skin 2. The side of the support 10 provided with the electrochemical sensor is on the opposite side from the side against the skin 2. The fibrous body 4 has a portion in contact with the skin and a portion that covers the side of the support comprising the electrochemical sensor. In other words, the fibrous body 4 straddles the skin and the electrochemical sensor. In this embodiment, the fibrous body comprises cotton or a nonwoven material.

With reference to FIG. 8, a second arrangement of the fibrous body 4 and of the sensing element 5 is illustrated. The fibrous body 4 sandwiches the sensing element. As a result, a portion of the fibrous body 4 is positioned against the skin. Next the sensing element 5 is positioned on the fibrous body portion against the skin. The portion of the fibrous body 4 which is not positioned on the skin is folded back over the sensing element 5 thus covering the sensor.

According to a first embodiment, the electrochemical sensor 14 comprises three electrodes as illustrated schematically in FIG. 9: a reference electrode 20, a working electrode 21 and an auxiliary electrode 22. The reference electrode 20 is a silver chloride (AgCl) electrode, the auxiliary electrode 22 is a platinum (Pt) electrode and the working electrode 21 is an electrode based on platinum black. The working electrode 21 has the shape of the disk. This disk is partially surrounded by the reference and auxiliary electrodes, the reference electrode being opposite the auxiliary electrode. The dimensions of the electrochemical sensor are of the order of a millimeter.

According to a second embodiment illustrated in FIG. 10, the electronic sensor comprises a reference electrode 20, a working electrode 21 and an auxiliary electrode 22. The reference electrode 20 is a silver chloride (AgCl) electrode, the auxiliary electrode 22 is a platinum (Pt) electrode and the working electrode 21 is an electrode based on platinum black. The working electrode 21 has the shape of a disk. This disk is partially surrounded by the reference and auxiliary electrodes. The electrodes are arranged concentrically: the working electrode 21 is partially surrounded by the reference electrode 20, and the reference electrode 20 is itself surrounded by the auxiliary electrode 22. The dimensions of the electrochemical sensor are of the order of a millimeter.

The electrochemical sensor of FIG. 9 or 10 may be used in a microhydraulic circuit illustrated schematically in FIG. 11.

In FIG. 11, the fibrous body 4 absorbs the biological liquid, here sweat, and transports it to three microchannels 15 marked out in a planar support 10. These microchannels 15 will each convey the sweat to sensing units 16, 17, 18. In the example represented, there is one sensing unit per microchannel 15. The sensing unit 16 will detect nitric oxide, the sensing unit 17 will detect nitrite contained in the sweat, and the sensing unit 18 will detect hydrogen peroxide contained in the sweat. Nitrite is mainly produced in the cells by the reaction between superoxide oxygen ($O2^{-*}$) and nitric oxide. The detection of $NO_2$- therefore makes it possible to have a better measurement of the NO concentration.

Thus, each sensing unit is devoted to the detection of a chemical species. Each sensing unit is electrically powered thus each sensing unit is at a potential imposed in order to carry out a stationary measurement. The sensing unit 18 is at the redox potential of hydrogen peroxide (oxidizing species) in order to detect hydrogen peroxide. The processing of the data from the sensing unit 18 will give the amount of $H_2O_2$. The sensing unit 16 is at the redox potential of NO (oxidizing species) in order to detect NO. Owing to the fact that the redox potential of $H_2O_2$ is lower than the redox potential of NO, the sensing unit 16 detects $H_2O_2$ as well as NO. The processing of the data from the sensing unit 18 will give the amount of $H_2O_2$ and NO taken together. The sensing unit 17 is at the redox potential of nitrite (oxidizing species) in order to detect NO. As the redox potential of $NO_2$- is above the redox potential of $H_2O_2$ and NO, the unit 17 detects $H_2O_2$ and NO as well as $NO_2^-$. The processing of the data from the sensing unit 18 will give the amount of $H_2O_2$, NO and $NO_2^-$ taken together. Another subsequent processing of the data produced by the sensing units 16, 17, 18 makes it possible to determine, by the difference, the amounts of each of the chemical species, i.e. of NO, $H_2O_2$ and $NO_2$-.

Alternatively, use may be made of a pulse method, each sensing unit will then be capable of detecting each species. After processing of the data, the amount of each species present will be able to be determined.

With reference to FIG. 12, the sensing element 5 comprises three microchannels 30, 31, 32 marked out in the thickness of the insulating planar support 10. The sensing units 16, 17 and 18 are placed on each bottom wall of the microchannels 30, 31, 32. The sensing unit 16 is configured to detect nitric oxide, the sensing unit 17 is configured to detect nitrite contained in the sweat, and the sensing unit 18 is configured to detect hydrogen peroxide contained in the sweat. Each sensing unit 16, 17, 18 comprises three sensors 14. A filter 29 is placed on top of the insulating planar support. The filter covers the microchannels. Finally a fibrous body 4 is placed on the filter 29.

The fibrous body 4 absorbs the biological liquid, here sweat, and transports it to the three microchannels 30, 31, 32 by means of capillary forces. When the sweat drained by the fibrous body 4 arrives level with the microchannels, the sweat is filtered by the filter 29 to remove certain interfering elements, then it is transported by the microchannels 30, 31, 32 at least up to the sensing units 16, 17, 18. The sensors of the sensing unit 16 then detect the NO, the sensors of the sensing unit 17 detect the nitrite and the sensors of the sensing unit 18 detect the hydrogen peroxide.

In one embodiment that is not shown, when the sensing element comprises several sensing units, at least one of which is devoted to the detection of a chemical species other than NO, for example hydrogen peroxide, then the filter 29 can be eliminated.

The current intensities that are obtained with the device according to invention are between the picoampere and the milliampere range.

Although the invention has been described in connection with several particular embodiments, it is quite obvious that it is in no way limited thereto and that it includes all the technical equivalents of the means described and also the combinations thereof provided that they fall within the scope of the invention.

The use of the verb "have", "comprise" or "include" and the conjugated forms thereof do not exclude the presence of elements or steps other than those mentioned in a claim.

In the claims, any reference sign between parentheses should not be interpreted as a limitation of the claim.

The invention claimed is:

1. A process for detecting, in a subject, an amount of NO produced by said subject in the course of a sequence of a predefined activity state, wherein an investigation zone of an epidermis of said subject is chosen, the production of NO dissolved in a biological liquid originating from the epidermis is tracked therein, directly and continuously, by means of a device formed of a first part, positioned on said investigation zone and held thereon in a leak-tight manner, this first part being attached to a sensing element, wherein the sensing element comprises an electrochemical sensor in a sensing unit, wherein the sensing unit carries out the detection of NO by means of an electrochemical sensor, wherein, owing to an energy generator associated with said sensing element, signals are sent by the electrochemical sensor, the reading of which signals enables the desired detection, wherein the electrochemical sensor provides the signal as a result of electrochemical measurements taken using the biological liquid produced by the subject in the investigation zone as electrolyte between two working electrodes positioned on an insulating planar support, wherein the working electrodes of the electrochemical sensor consist of metal deposits of platinum black, and wherein the process further comprises monitoring bioavailability of L-arginine based on the detection of NO.

2. The process as claimed in claim 1, wherein the biological liquid is sweat.

3. The process as claimed in claim 1, wherein the sensing element comprises a plurality of sensing units that carry out a detection of NO by electrochemical sensors to obtain a cutaneous map of NO production within the investigation zone, in which the plurality of sensing units includes the first sensing unit.

4. The process as claimed in claim 1, wherein the process further comprises detecting at least one parameter associated with a physiological state or a pathology, wherein the parameter corresponds to an integral of a graph, into which the signal sent by the first electrochemical sensor has been converted, between a start time and an end time.

5. The process as claimed in claim 4, in which the at least one parameter is associated the bioavailability of L-arginine.

6. The process as claimed in claim 1, wherein the electrochemical sensor is a first electrochemical sensor and the sensing unit is a first sensing unit, wherein the sensing element comprises a second electrochemical sensor distributed in a second sensing unit, wherein the second sensing unit carries out the detection of NO2- by means of the second electrochemical sensor.

7. The process as claimed in claim 6, wherein the sensing element comprises a third electrochemical sensor distributed in a third sensing unit, wherein the third sensing unit carries out a detection of $H_2O_2$ by said third electrochemical sensor.

8. The process as claimed in claim 6, wherein the second sensing unit is at the redox potential of $NO_2$- and the first sensing unit is at the redox potential of NO, the process further comprises processing data produced by the first and second sensing units to determine, by a difference thereof, amounts of NO and $NO_2$-.

9. The process as claimed in claim 6, wherein the sensing element comprises a third electrochemical sensor distributed in a third sensing unit, wherein the third sensing unit carries out the detection of H2O2 by said third electrochemical sensor, in which the third sensing unit is at the redox potential of $H_2O_2$ in order to detect hydrogen peroxide, the second sensing unit is at the redox potential of $NO_2$- and the first sensing unit is at the redox potential of NO, wherein the process further comprises processing data produced by the first, second and third sensing units to determine, by a difference thereof, amounts of $H_2O_2$, NO and $NO_2$.

10. The process as claimed in claim 1, wherein the first part comprises a fibrous body in order to convey the biological liquid from the investigation zone to the sensing element by means of capillary forces.

11. The process as claimed in claim 10, wherein the fibrous body is attached to the sensing element and surmounts the sensing element.

12. The process as claimed in claim 1, wherein a reference electrode is connected to the two working electrodes.

13. The process as claimed in claim 1, wherein the insulating planar support comprises at least one microchannel so as to guide the biological liquid to the electrochemical sensor.

14. The process as claimed in claim 1, wherein the sensing element comprises a plurality of similar electrochemical sensors, the signals of which are combined to improve the output signal.

15. The process as claimed in claim 1, wherein the pattern of the working electrodes relative to their support follows a Hilbert curve in order to improve the strength of the output signal per unit area of the support.

16. The process as claimed in claim 1, wherein the measurements are carried out in line with orifices provided in the planar support, which is in line with the conductive patterns of the electrodes.

17. The process as claimed in claim 1, wherein the sensing element comprises a plurality of electrochemical sensors distributed in a plurality of sensing units, and in that each sensing unit is configured to detect at least one chemical species.

18. The process as claimed in claim 1, wherein the insulating planar support comprises a plurality of microchannels, and wherein each microchannel comprises a said sensing unit.

19. The process as claimed in claim 1, wherein the first part further comprises a eugenol membrane configured to filter the biological liquid at an inlet of the sensing element in order to avoid distorting the detection of NO by interfering elements contained in the biological liquid.

20. The process as claimed in claim 1, wherein a second part is positioned above the first part, the second part containing electronics for receiving the raw measurements from the electrochemical sensor, for converting them into an NO concentration and ensuring the transmission of the signal with other parameters linked to the environment.

21. The process as claimed in claim 1, wherein the device comprises a gyroscopic and/or accelerometric unit to detect the activity state of the subject and wherein the device is configured to carry out and transmit measurements at a frequency that is a function of the activity state of the subject.

* * * * *